United States Patent [19]
Drouin et al.

[11] Patent Number: 5,972,033
[45] Date of Patent: Oct. 26, 1999

[54] HIP JOINT PROSTHESIS HAVING A 22.22 MM ZIRCONIA FEMORAL HEAD AND A 12/14 SIZE STEM

[75] Inventors: Jean-Michel Drouin; Bernard Cales, both of Evreux, France

[73] Assignee: Norton Desmarquest Fine Ceramics, Evreux, France

[21] Appl. No.: 08/919,486

[22] Filed: Aug. 28, 1997

Related U.S. Application Data

[63] Continuation of application No. 08/724,335, Oct. 1, 1996, abandoned.

[51] Int. Cl.$^6$ .......................................................... A61F 2/34
[52] U.S. Cl. .................................................................. 623/23
[58] Field of Search .................................. 623/16, 18, 22, 623/23

[56] References Cited

U.S. PATENT DOCUMENTS

| | | | |
|---|---|---|---|
| 4,636,218 | 1/1987 | Fukuura et al. | 623/23 |
| 4,964,869 | 10/1990 | Auclair et al. | 623/23 |
| 5,181,929 | 1/1993 | Prats et al. | 623/23 |
| 5,362,311 | 11/1994 | Amino et al. | 623/22 |
| 5,413,610 | 5/1995 | Amino et al. | 623/23 |

FOREIGN PATENT DOCUMENTS

| | | | |
|---|---|---|---|
| 2636837 | 9/1989 | France | A61F 2/32 |
| 2689390 | 5/1991 | France | A61F 2/36 |
| WO 89/10337 | 11/1989 | WIPO | C04B 35/04 |
| WO 97/31592 | 9/1997 | WIPO | A61F 2/30 |

OTHER PUBLICATIONS

Drouin, J. M. and Cales, B., "Yttria–Stabilized Zirconia Ceramic for Improved Hip Joint Head", Bioceramics, vol. 7 Edited by O.H. Andersson and A. Yli–Urpo, (Proceedings of the 7th International Symposium on Ceramics in Medicine, Turku, Finland, Jul. 1994) pp. 389–394.

*Primary Examiner*—David J. Isabella
*Attorney, Agent, or Firm*—Thomas M. DiMauro

[57] ABSTRACT

The invention relates to a ceramic hip joint prosthesis head for use with a trunnion, the trunnion having a frustoconical end comprising a first section having a diameter of about 12 mm which expands inward at a total angle of about 6 degrees to form a second section having a diameter of about 14 mm, wherein each head comprises:

a) a substantially spherical outer diameter of about 22.22 mm, b) a centerpoint, and c) a recess which forms a taper wall extending inward from the outer diameter of the head, wherein the taper wall has a shape suitable for taper fitting upon the frustoconical end of the trunnion to produce contact between the taper wall and the first section of the frustoconical end of the trunnion, a perimeter being defined by the deepest contact between the taper wall and the first section of the frustoconical end of the trunnion, the perimeter having a centerpoint, and wherein each head, when taper fit upon the frustoconical end of the trunnion, has a rupture load of at least 46 kN and is characterized by a distance D between a) the centerpoint of the head and b) the centerpoint of the perimeter defined by the deepest contact between the taper wall and the first section of the frustoconical end of the trunnion first section of the frustoconical end of the trunnion, wherein D has an absolute value of less than 3 mm.

22 Claims, 11 Drawing Sheets

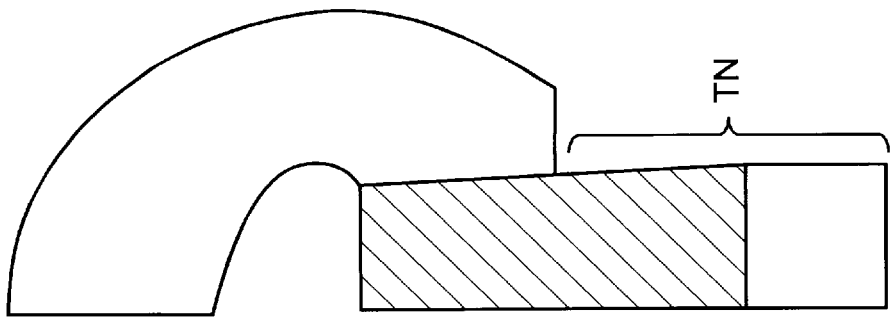
FIG. 1C LONG NECK
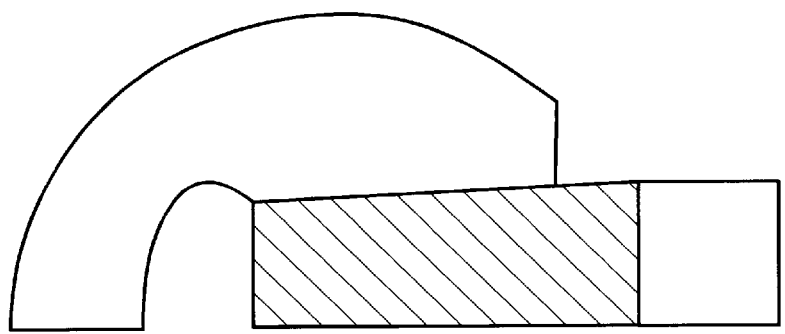
FIG. 1B MEDIUM NECK
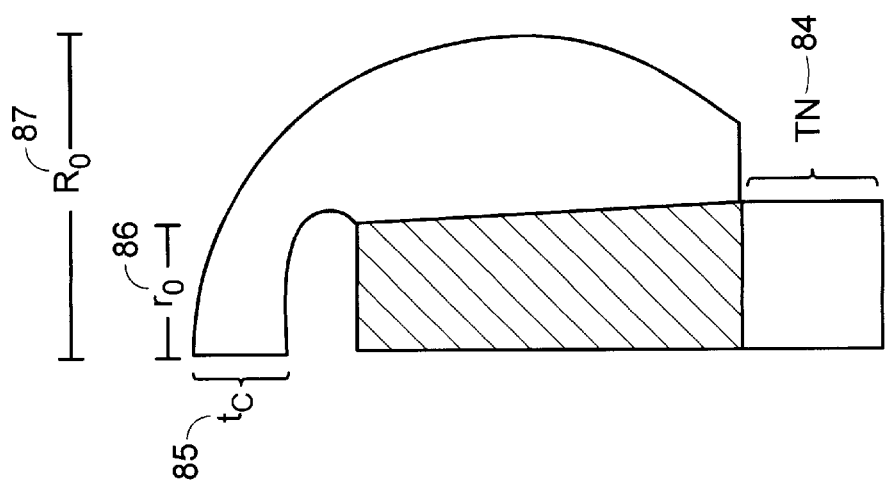
FIG. 1A SHORT NECK

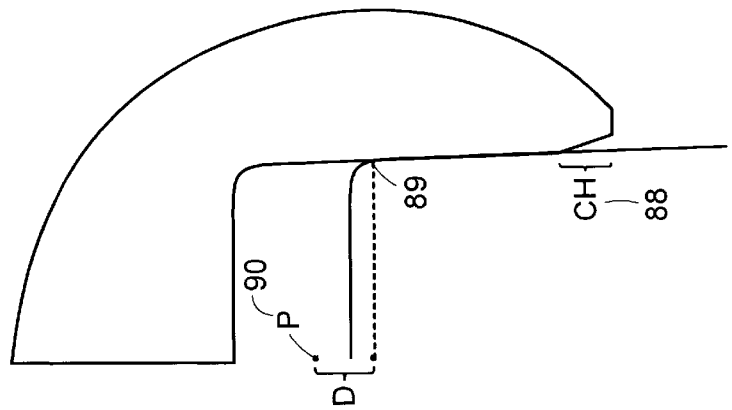
FIG. 2D (+3)
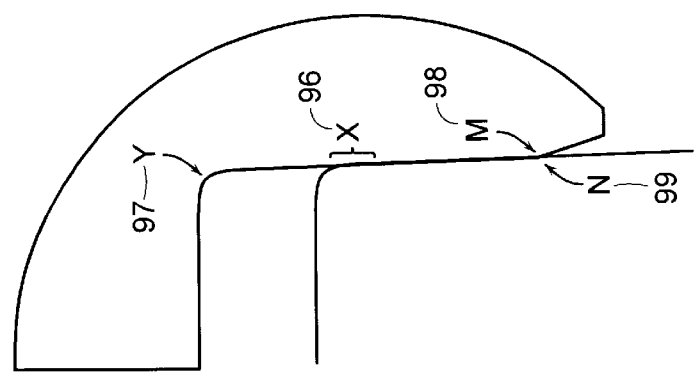
FIG. 2C (+2)
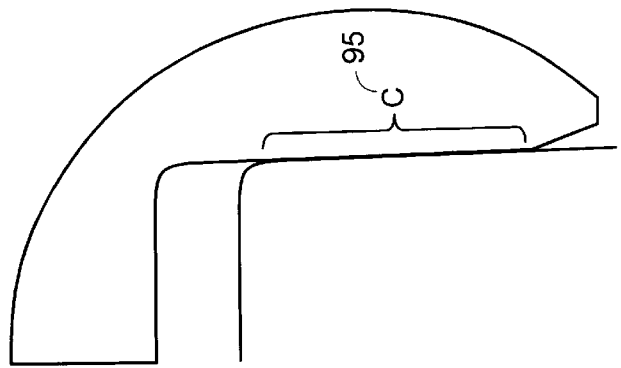
FIG. 2B (0)
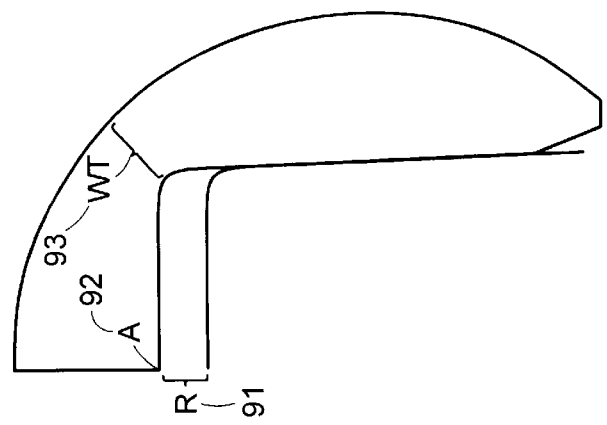
FIG. 2A (-1)

HIP JOINT PROSTHESIS HAVING A 22.22 MM ZIRCONIA FEMORAL HEAD AND A 12/14 SIZE STEM

This application is a continuation of application Ser. No. 08/724,335, filed Oct. 1, 1996, now abandoned.

BACKGROUND OF THE INVENTION

In surgeries requiring a total hip joint replacement, the upper portion of the femur must be replaced and an appropriate material must be selected for each modular replacement component. Over the past 25 years, a number of replacement materials have been identified for use as the femoral head component. In particular, modular metallic and alumina head components have been extensively studied. However, the metallic components are highly susceptible to corrosion and the alumina components typically have a flexural strength of only about 600 MPa. The low strength of alumina heads is particularly problematic for 22.22 mm diameter designs, as they historically have failed to safely exceed the FDA goal that the head be able to withstand a rupture load of 46 kN.

Because of its superior flexural strength of at least 900 MPa, yttria stabilized zirconia polycrystal ("YTZP") has been selected by the medical community for use in artificial hip joint prosthesis heads, and has even been used in 22.22 mm heads to attain rupture load of at least 60 kN.

Although 22.22 mm YTZP heads have attained the rupture load desired by the FDA, they have generally only done so when fitted with metallic stems having diameters of only 8 mm to 10 mm. Unfortunately, the medical community routinely uses much larger diameter stems (e.g., the Euro-cone having a "12/14" diameter stem) during hip joint surgery. One very popular stem is the "Euro-cone", whose frustoconical portion has a 12 mm end which enlarges to a 14 mm end at a total angle of about 6 degrees (typically between about 5 37'37" and 5 43'30"). Since modularity and interchangeability are valued attributes in hip joint replacement surgery, and the 22.22 mm zirconia head binds the surgeon to an unconventionally small diameter stem, surgeons have been reluctant to adopt these heads. Accordingly, widespread use of the 22.22 mm zirconia head has been limited.

Another concern in designing hip joint prosthesis heads is the ability to tailor the overall length of the head-trunnion combination to the needs of the particular patient which can only be determined at the time of surgery. In modern prosthesis systems, flexibility in length is provided by holding the trunnion length constant and designing a set of same diameter ceramic heads to slide upon the trunnion stem with varying degrees of recess penetration. The heads within a particular set often produce differences in overall head-trunnion length of at least 3 mm, and are typically identified as "short neck", "medium neck" or "long neck" heads. The "short neck" head of a set has a deep, wide cavity designed for deep stem penetration and takes its name from the short length of trunnion neck 84 visible after stem penetration. See FIG. 1a. Conversely, the "long neck" head of a set has a shallow, narrow cavity for shallow stem penetration and takes its name from the long length of trunnion neck visible after stem penetration. See FIG. 1c.

Therefore, there is a great need to develop a kit of short, medium and long neck 22.22 mm zirconia heads differing by at least 3 mm in neck length which can fit on a standard 12/14 stem and attain rupture loads of at least 46 kN.

The strength of a volume of material is typically determined by the size and frequency of its intrinsic and extrinsic flaws. Intrinsic flaws are those found throughout the microstructure of the material and typically include agglomerates, inclusions and porosity. Intrinsic flaws may be in the volume of the material or on its surface. Extrinsic flaws are typically introduced by machining and grinding damage, and so are found only at or near the surface of the material.

The tensile strength of YTZP zirconia is known to be a function of flaw size and the degree of yttria stabilization. Noguchi et al., *J. Am. Cer. Soc.* 73 (9) 2667–76 (1990), found the mean tensile strengths of pressureless sintered YTZP's to range from 430 MPa to 550 MPa and hot isostatically pressed ("hipped") YTZP's to range from 570–745 MPa.

When the stress upon a particular volume of ceramic material exceeds the tensile strength of that volume, the material ruptures. Therefore, in designing a ceramic hip joint prosthesis head, it is helpful to understand the stresses which act upon the head and the factors which determine the strength of the head. When the recess of a head is press fit onto the metallic stem, the metallic stem undergoes a plastic deformation and pushes laterally against the taper wall of the recess. Two types of tensile stresses develop in the ceramic material from this action. The first is a hoop stress which acts outwardly upon ceramic material ringing the stem. The second is a crown stress which acts upon the upper corners of the recess and is caused by the directionally opposing hoop stresses on opposing sides of the taper wall. Hoop stresses are also present at the upper corners of the head recess, often reaching over 80% of the associated crown stress.

Fessler, *Proc. Instn. Mech. Engrs.* Vol 203 Part H, 1989, pp.15–31, extensively studied the stresses in conventional heads and found it reasonable to expect that the maximum tensile stress values would occur in the inner crown surface and not elsewhere.

Fessler characterized each head by outer radius Ro 87 and a centerline recess radius ro 86, and found that conventional heads typically possess ro/Ro values of between 0.30 and 0.47. See FIG. 1a. Fessler also taught an optimum ro/Ro value of about 0.37.

SUMMARY OF THE INVENTION

In accordance with the present invention, there is provided a kit comprising a plurality of ceramic hip joint prosthesis heads for use with a trunnion, the trunnion having a frustoconical end comprising a first section having a diameter of about 12 mm which expands inward at a total angle of about 6 degrees to form a second section having a diameter of about 14 mm, wherein each head comprises:

a) a substantially spherical outer diameter of about 22.22 mm, b) a centerpoint, and c) a recess which forms a taper wall extending inward from the outer diameter of the head, wherein the taper wall has a shape suitable for taper fitting upon the frustoconical end of the trunnion to produce contact between the taper wall and the first section of the frustoconical end of the trunnion, a perimeter being defined by the deepest contact between the taper wall and the first section of the frustoconical end of the trunnion, the perimeter having a centerpoint, wherein each head, when taper fit upon the frustoconical end of the trunnion, has a rupture load of at least 46 kN and is characterized by a distance D between a) the centerpoint of the head and b) the centerpoint of the perimeter defined by the deepest contact between the taper wall and the first section of the frustoconical end of the trunnion, and
wherein the range of values of D within the kit is at least 3 mm.

Also in accordance with the present invention, there is provided a ceramic hip joint prosthesis head for use with a trunnion, the trunnion having a frustoconical end comprising a first section having a diameter of about 12 mm which expands inward at a total angle of about 6 degrees to form a second section having a diameter of about 14 mm, wherein the head comprises:

a) a substantially spherical outer diameter of about 22.22 mm, b) a centerpoint, and c) a recess which forms a taper wall extending inward from the outer diameter of the head, wherein the taper wall has a shape suitable for taper fitting upon the frustoconical end of the trunnion to produce contact between the taper wall and the first section of the frustoconical end of the trunnion, a perimeter being defined by the deepest contact between the taper wall and the first section of the frustoconical end of the trunnion, the perimeter having a centerpoint, wherein each head, when taper fit upon the frustoconical end of the trunnion, has a rupture load of at least 46 kN and is characterized by a distance D between a) the centerpoint of the head and b) the centerpoint of the perimeter defined by the deepest contact between the taper wall and the first section of the frustoconical end of the trunnion, and wherein D has an absolute value of less than 2 mm.

In preferred embodiments, the ceramic comprises at least about 80 mol % zirconia, and preferably consists essentially of zirconia partially stabilized by between about 2 mol % and 5 mol % rare earth oxide, and having a four point flexural strength of at least 920 MPa, preferably at least 1300 MPa.

In some special embodiments wherein the trunnion is Cr-Co, the upper corner of the recess is polished to a surface roughness Ra of less than 0.2 um (preferably about 0.1 um) to improve the burst strength of the heads.

In some other special embodiments wherein the trunnion is Ti alloy, the taper wall is polished to a surface roughness Ra of less than 0.2 (preferably about 0.1 um) to improve the burst strength of the heads.

In other special embodiments wherein the trunnion is Ti alloy and the head recess includes a chamfer adjacent the outer diameter of the head, the inner most portion of the chamfer is rounded to a radius of between 5 mm and 400 mm and smoothed to improve the cyclic fatigue strength of the heads.

DESCRIPTION OF THE FIGURES

FIGS. 1a–c present the right side of axial cross-sections of long neck, medium neck and short neck ceramic heads fit upon the same conventional trunnion frustocone.

FIGS. 2a–d presents the right sides of axial cross-sections of four 22.22 mm zirconia head geometries suitable for fitting upon the same 12/14 frustocone of a trunnion.

DETAILED DESCRIPTION OF THE PRESENT INVENTION

Figure 3A:
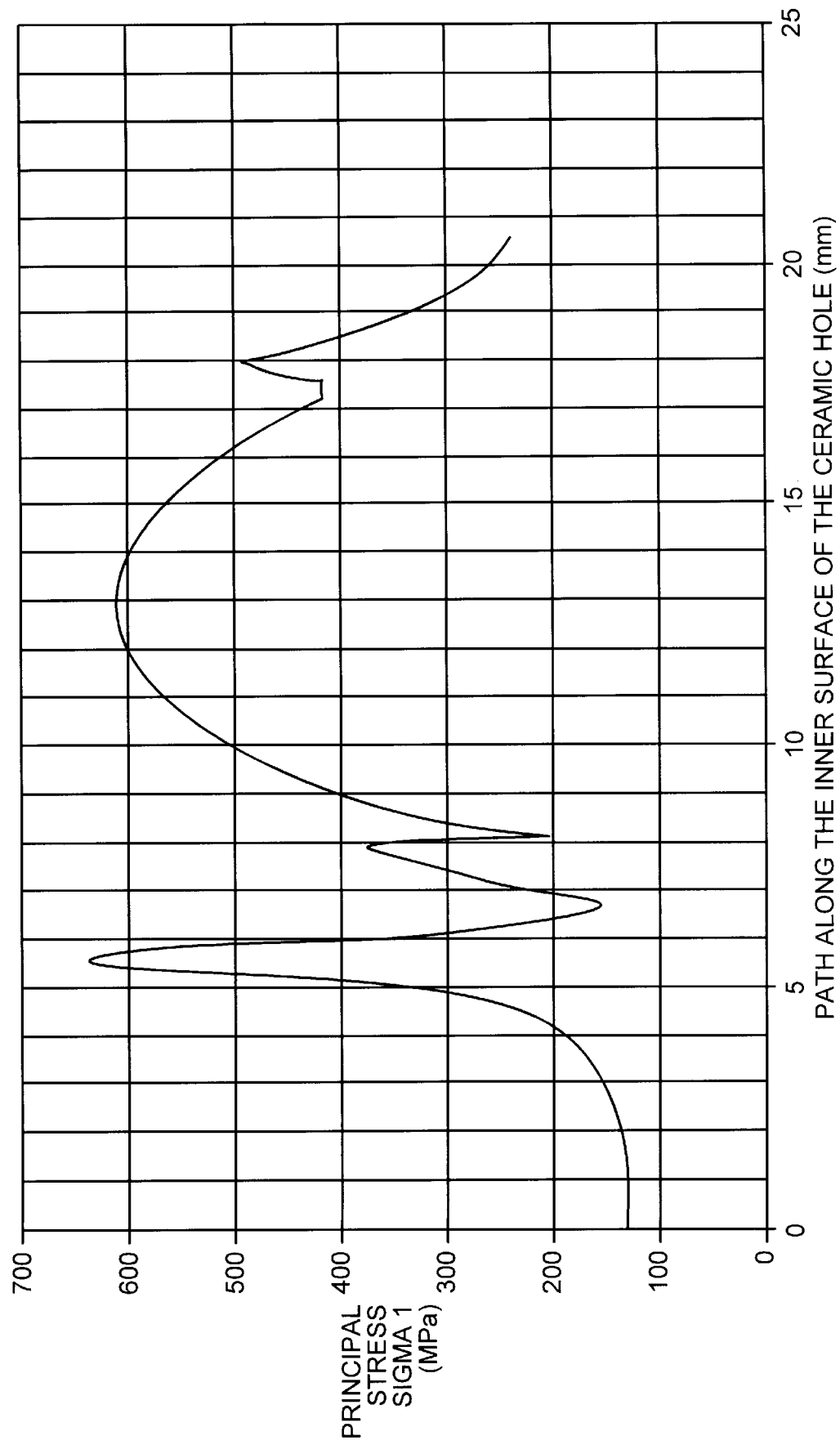
FIGS. 3a–d are graphs of the predicted stress maxima along the recess surface of the heads of FIGS. 2a–d when fit to a 12/14 titanium alloy frustocone, as predicted by FEA, wherein "0 mm" corresponds to the top center of the head recess (designated as 92 in FIG. 2a) and "20 mm" corresponds to the bottom of the head recess (designated as 94 in FIG. 2a).
Figure 3B:
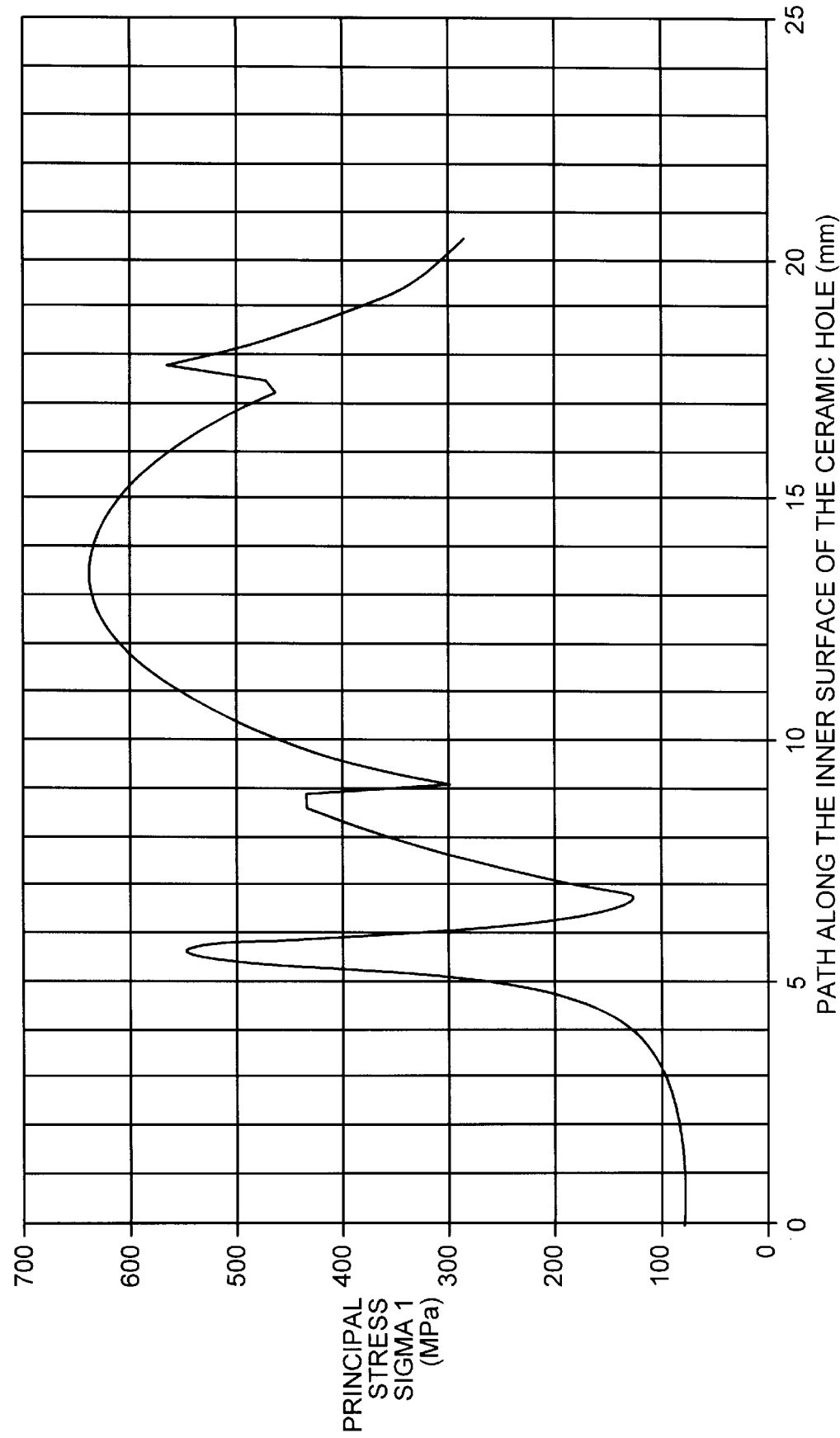
Figure 3C:
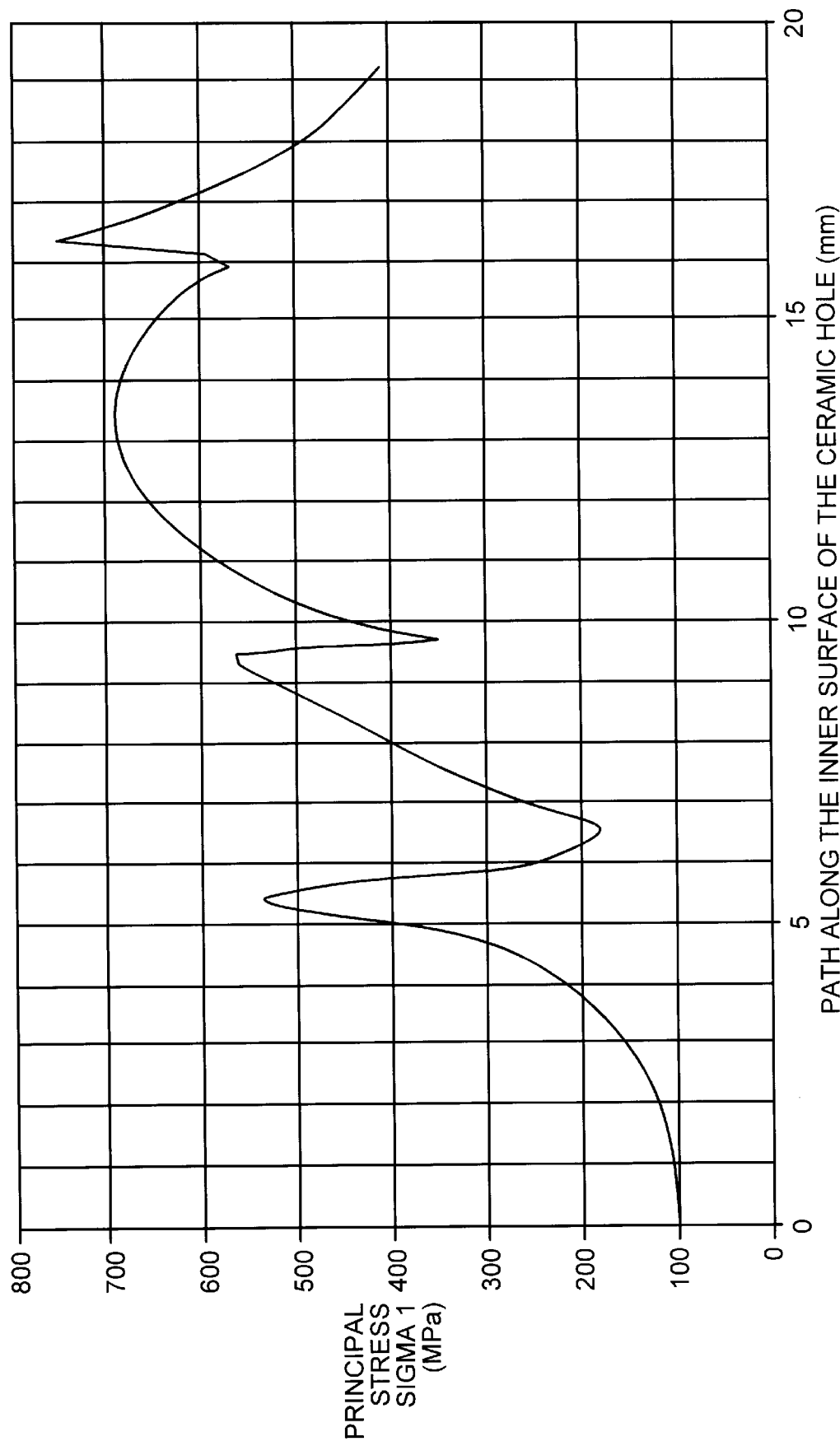
Figure 3D:
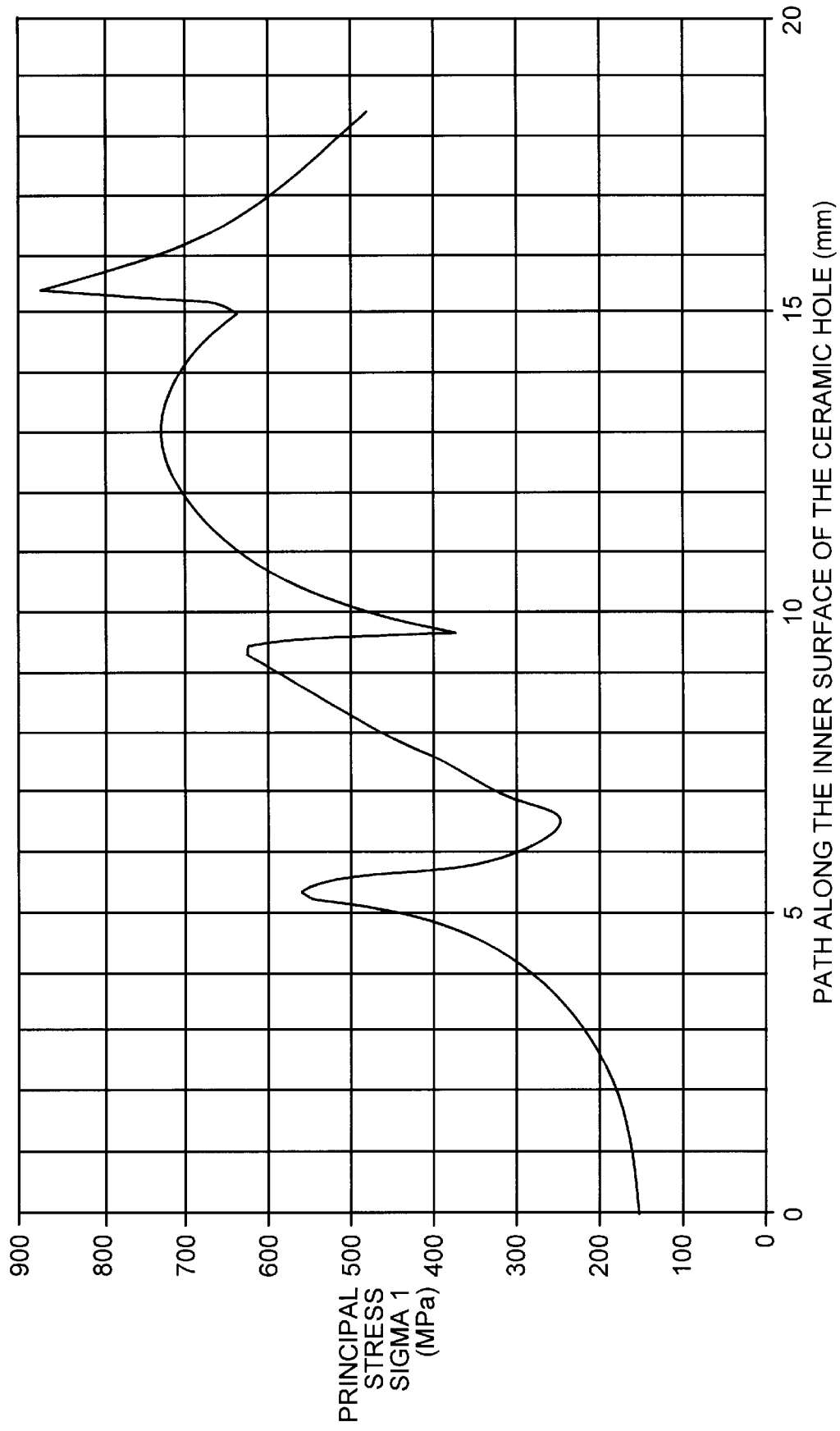
Figure 4A:
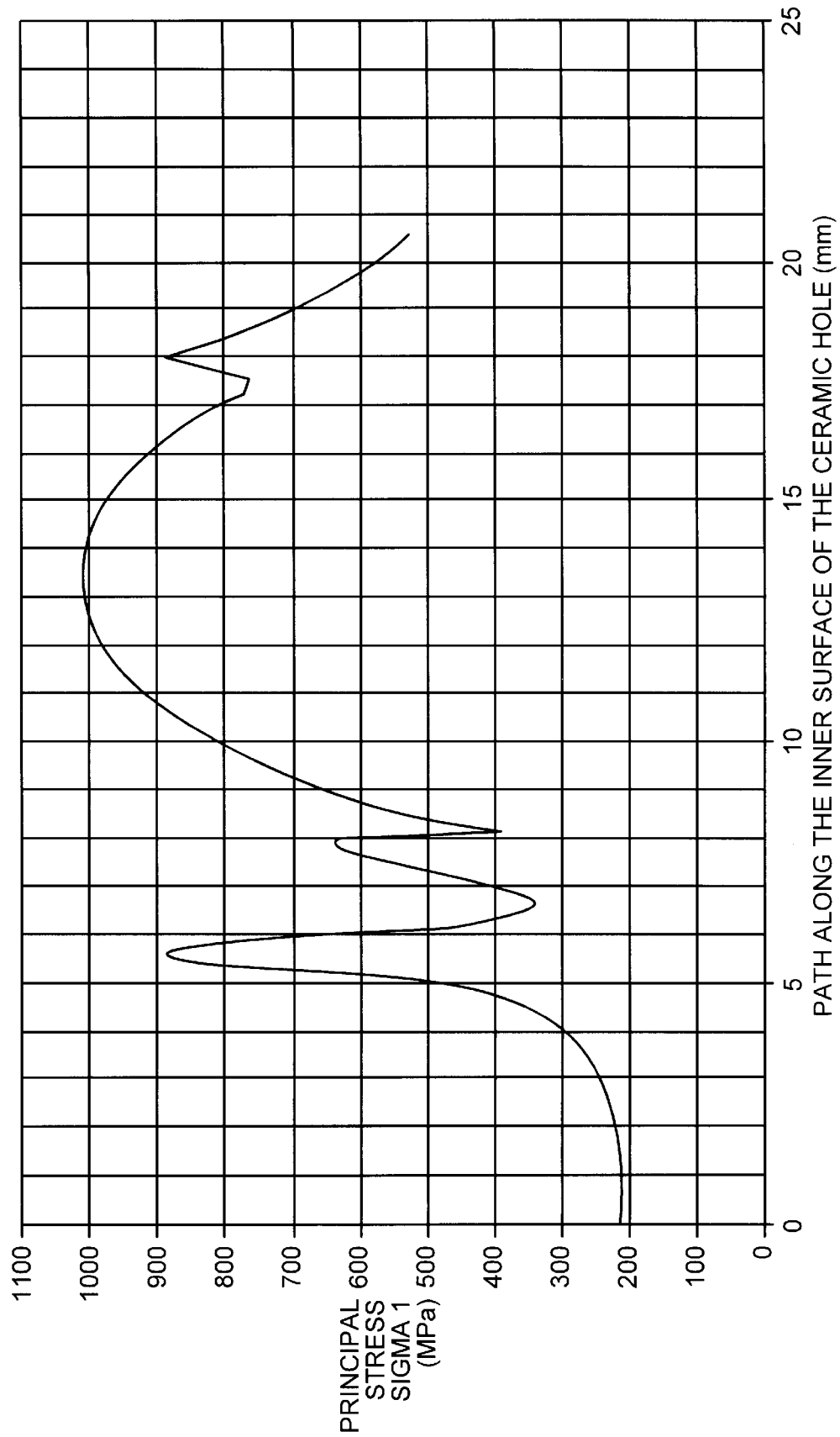
FIGS. 4a–d are graphs of the predicted stress maxima along the recess surface of the heads of FIGS. 2a–d when fit to a 12/14 chrome-cobalt frustocone, as predicted by FEA.
Figure 4B:
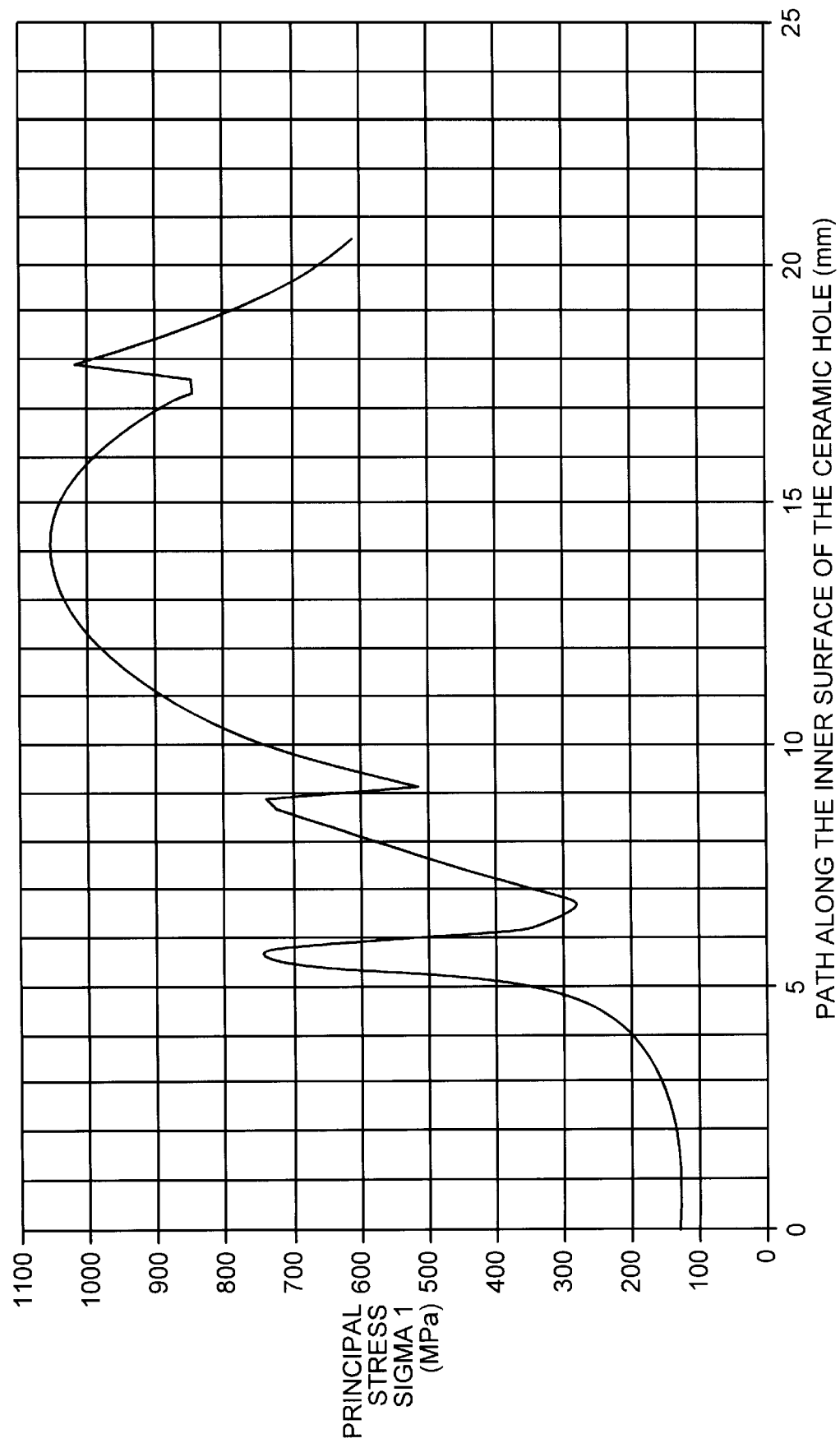
Figure 4C:
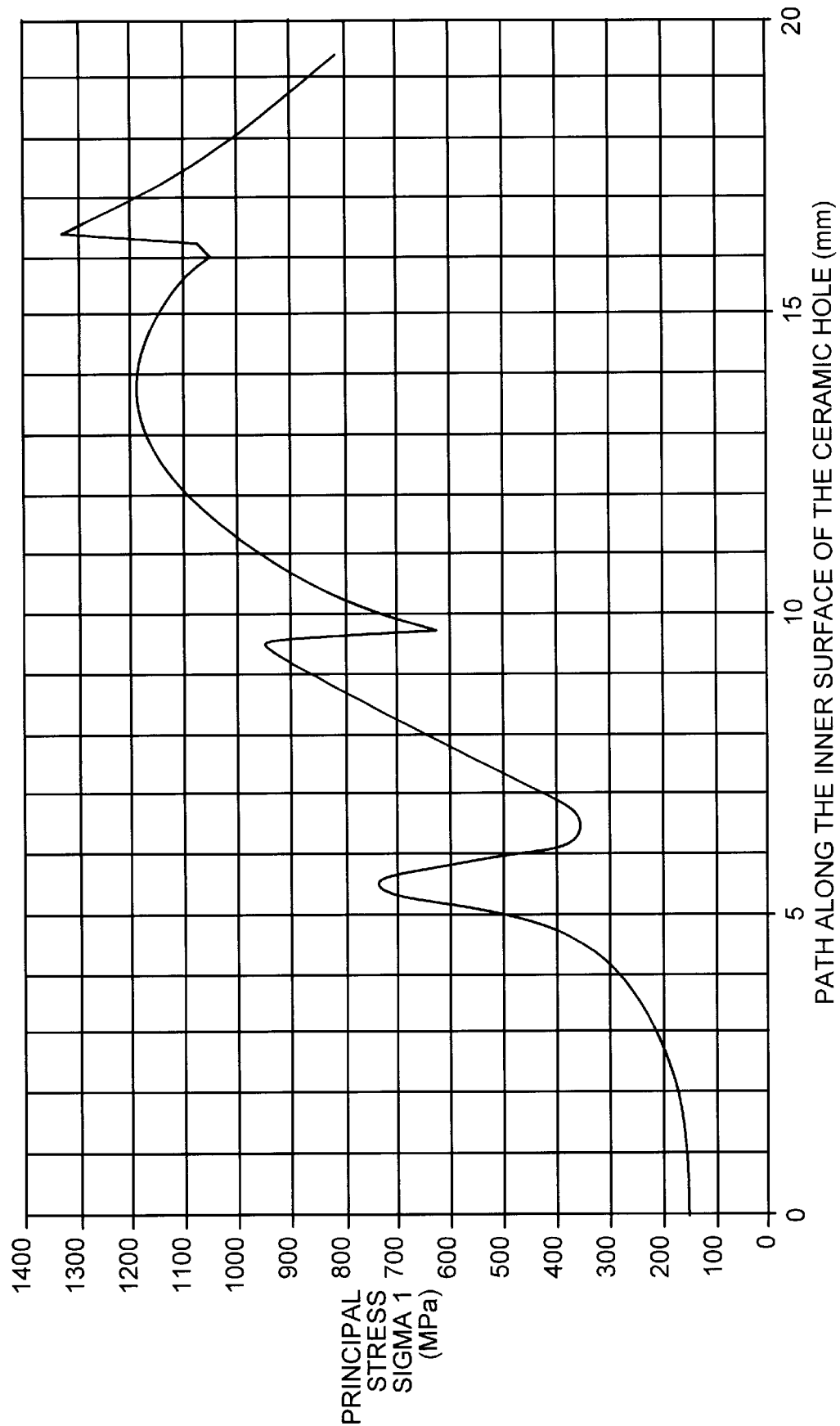
Figure 4D:
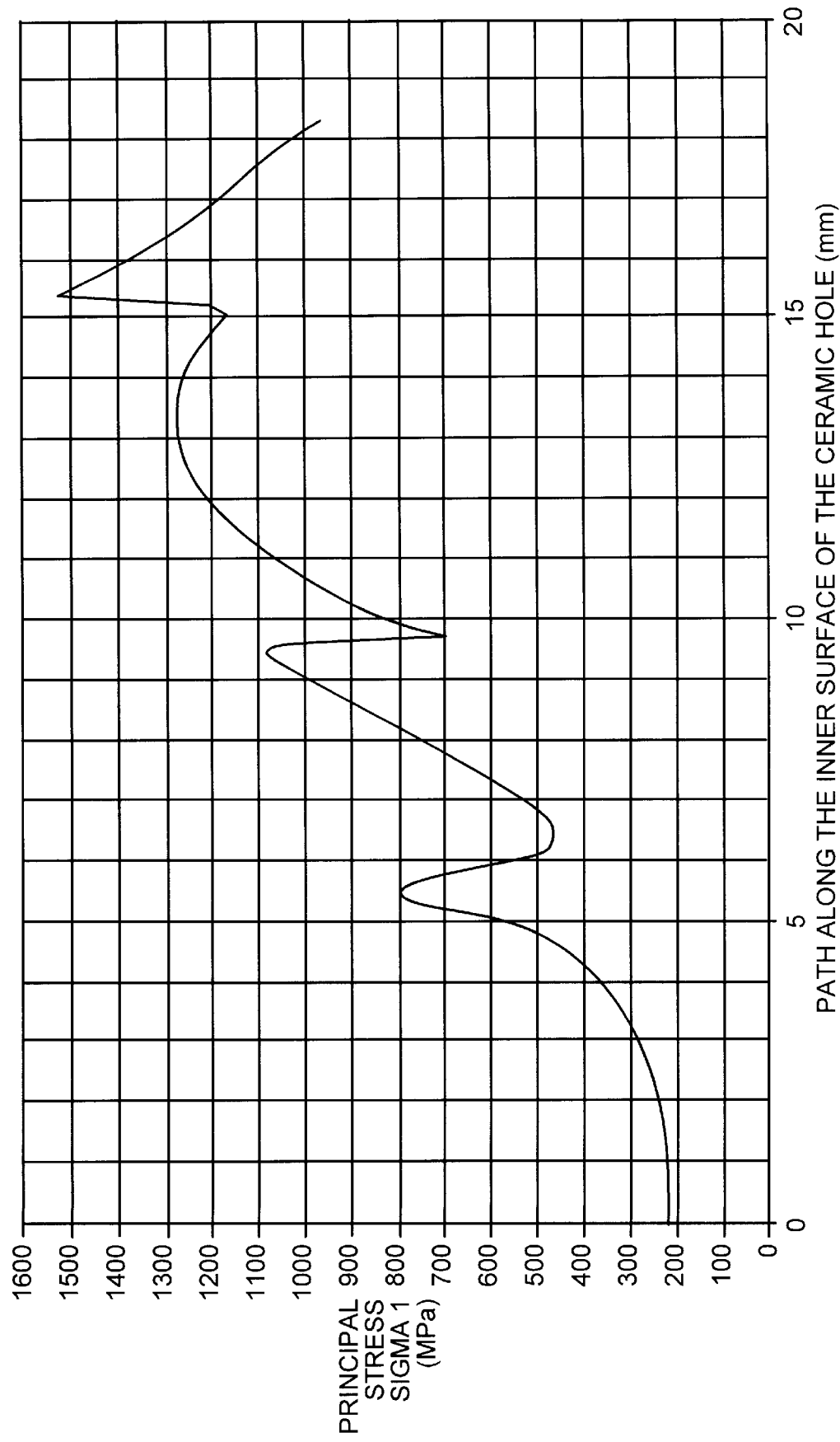

For the purposes of the present invention, when the deepest contact between the frustocone end of the trunnion and the taper wall of the head recess is at a point beyond the centerpoint of the head, the D value is considered to be positive. When deepest contact between frustocone end of the trunnion and the taper wall of the recess stops prior to the centerpoint of the head, the D value is considered to be negative.

Designs for the heads of the present invention were developed under a number of constraints. First, as mentioned above, the head diameter was set at 22.22 mm and the recess therein was shaped to accommodate a 12/14 Eurocone stem. Second, the stem roughness was set at an Rmax of about 30 um to represent a very high surface roughness in a commercial stem. Third, the head material was a YTZP having about 3.0 mol % yttria, a flexural strength of at least 920 MPa, and an elastic modulus of about 220 GPa. One YTZP meeting these characteristics is available from Ceramiques Techniques Desmarquest of Evreux, France under the trademark PROZYR. Fourth, the stem material was selected to be Ti alloy having an elastic modulus of about 115 GPa. Lastly, the kit to be developed needed to have a range of D values of at least 3 mm.

The head designs take into account the effect of a number of geometric variables. In particular, the designs optimize 1) the length of the reserve (designated as 91 in FIG. 2a), 2) the wall thickness (designated as 93 in FIG. 2a) between the crown and the head outer diameter, 3) the contact area (shown as a length 95 in FIG. 2b) between the head and the stem, and 4) the chamfer height (designated as 88 in FIG. 2d). Reserve length and wall thickness are maximized in order to minimize stresses at the crown corner (designated as 97 in FIG. 2c). Contact area is maximized to reduce the average taper pressure along the recess taper wall. Chamfer height is maximized to reduce stresses at the bottom of the head. Since each of these variables can not be simultaneously maximized, tradeoffs are necessary. Accordingly, finite element analysis ("FEA") has been used to optimize head geometries. The FEA program essentially incorporates the mechanical principles outlined in Fessler, above.

The kit of heads resulting from the FEA effort is shown in FIGS. 2a–d. FIGS. 2a–d correspond to D values of +3.39 mm, +2.39 mm, +0.39 mm, and −0.61 mm, respectively, wherein D is the distance between the centerpoint of the head (designated as 90 in FIG. 2d), and b) the centerpoint of the perimeter defined by the deepest contact (designated as 89 in FIG. 2d) between the taper wall and the first section of the frustoconical end of the trunnion.

It can be seen from examination of the heads in FIGS. 2a–d that the inventive head is much thinner (i.e., ro/Ro is much larger) than a conventional head. Its centerline taper radius ro/Ro of about 0.56 produces hoop stresses which are much higher than the ro/Ro value of 0.37 suggested by Fessler. See FIG. 2a of Fessler.

When these geometries are subjected to theoretical loads of 45 kN (i.e., 1 kN below the FDA required mean rupture load), it is found that very high stresses are still present. The heads' predicted responses to loading upon 12/14 titanium alloy trunnions are shown in FIGS. 3a–d and summarized in Table I below:

TABLE I

| Figure and D Value (mm) | Maximum Principal Stress S1 (MPa) | Location | 2nd Highest Principal Stress S2 (MPa) | Location |
|---|---|---|---|---|
| 2a  +3.39 | 610 | 6 (point) | 605 | 13 (region) |
| 2b  +2.39 | 620 | 13 (region) | 560 | 18 (point) |
| 2c  +0.39 | 750 | 18 (point) | 700 | 13 (region) |
| 2d  −0.61 | 880 | 16 (point) | 730 | 13 (region) |

Since the maximum stress predicted to be generated by theoretically press fitting these heads onto a 12/14 titanium alloy stem exceeded the YTZP tensile strengths reported by Noguchi (i.e, 550 MPa for pressureless sintered YTZP and 745 MPa for hipped YTZP), it was at first believed that kits made from these designs would not meet the FDA criteria for the mean rupture load of 46 kN. In particular, none of the designs would prevent stresses exceeding the 550 MPa tensile strength of pressureless sintered YTZP, and only two of the heads designs would prevent stresses exceeding the 745 MPa tensile strength of hipped YTZP.

However, actual burst testing of hipped heads has shown these designs to be surprisingly robust. Burst testing was performed in substantial accordance with draft French Standard NFS 90443. Table II reports the mean rupture load for hipped YTZP heads having the designs shown in FIGS. 2a, 2c and 2d.

TABLE II

| Figure and D Value (mm) | Mean Rupture Load (kN) | Std. Deviation (kN) |
|---|---|---|
| 2a  +3.39 | 83.41 | 12.23 |
| 2c  +0.39 | 79.68 | 4.95 |
| 2d  −0.61 | 52.58 | 5.61 |

In a related test, a pressureless sintered YTZP 22.22 head having the design corresponding to FIG. 2b was found to have a rupture load of about 63 kN when loaded upon a 12/14 titanium alloy trunnion.

No matter what the reason for the unexpectedly good burst test results, the hipped YTZP heads having the designs of FIGS. 2a–d were found to each have mean rupture loads of at least 46 kN when press fit onto 12/14 stems made of Ti alloy. It is believed that this is the first kit of ceramic 22.22 mm heads having a commercially useful range of neck lengths which can meet the FDA rupture load requirement of 46 kN when fit upon a 12/14 stem.

When a zirconia head is taper fit to a titanium alloy (such as Ti-Al-4V) stem, the low elastic modulus of titanium allows for a relatively elastic response to loading, thereby causing the frustocone surface to push fairly evenly against the recess wall, so that the critical stress is usually an evenly distributed hoop stress along the surface of the recess taper wall. The taper walls of the heads used in the rupture load testing with Ti alloy trunnions were found to have a surface of roughness Ra of about 0.3–0.6 um. Related studies have suggested the critical flaws in hipped zirconia heads may be extrinsic flaws produced by surface roughnesses of about 0.3 um Ra and that polishing these regions to about 0.1 um Ra can strongly increase the rupture load. Accordingly, although not confirmed by actual testing, it is believed that polishing the taper walls of these heads to a surface roughness Ra of less than 0.2 um (preferably about 0.1 um) reduces the flaw size along the wall and increases the material strength, but without significantly increasing either the hoop or crown stresses due to greater axial displacement of the head upon the trunnion, and so a rupture load of at least 60 kN can be expected for each of the four head designs shown in FIGS. 2a–d when fitted to a titanium alloy trunnion.

Surprisingly, actual burst tests also gave excellent results when these same heads were fitted to Cr-Co trunnions. Usually, Cr-Co trunnions produce lower fracture loads than Ti alloy trunnions. The higher elastic modulus of the Cr-Co material (about 220 GPa) along with its higher yield strength (about 830 GPa) are believed to be the reason for the lower fracture load. When fitted with a zirconia head, the Cr-Co trunnion does not yield and conform to the head taper wall as readily as does a Ti trunnion. The high elastic modulus of Cr-Co allows the stem to sufficiently resist deformation upon press fitting so that only the upper part of the stem pushes on the taper wall. The result of this phenomenon is that the contact area is small and localized at the top of the trunnion (as shown by region 96 is FIG. 2c), and the stress is concentrated in the upper crown of the head (as shown by region 97 in FIG. 2c). Indeed, preliminary linear FEA of the heads of FIG. 2 upon 12/14 Cr-Co trunnions indicated much higher maximum stresses than for the Ti trunnion application. See FIGS. 4a–d and Table III.

TABLE III

| Figure and D Value (mm) | Highest Stress (MPa) | Location | 2nd Highest Stress (MPa) | Location |
|---|---|---|---|---|
| 2a  +3.39 | 1020 | 13 | 890 | 6 and 18 |
| 2b  +2.39 | 1070 | 14 | 1010 | 18 |
| 2c  +0.39 | 1340 | 16 | 1200 | 14 |
| 2d  −0.61 | 1520 | 15 | 1280 | 13 |

However, actual burst testing (as shown in Table IV below) reveal fracture loads well above 46 kN for the heads of FIGS. 2b and 2c, and a fracture load of nearly 42 kN for the head of FIG. 2a.

TABLE IV

| Figure and D Value (mm) | Mean Rupture Load (kN) | Std. Deviation (kN) |
|---|---|---|
| 2a  +3.39 | 41.94 | 4.03 |
| 2b  +2.39 | 55.12 | 4.20 |
| 2c  +0.39 | 55.81 | 4.33 |
| 2d  −0.61 | 39.46 | one head only |

Analysis of the failure origins of the head of FIG. 2a indicated that most of the failures occurred in the upper corner of the crown (as shown by region 97 in FIG. 2c), and that the surface roughness of the head recess in this region was moderately rough (about 0.3 um Ra). Because related studies have suggested that the critical flaws in hipped zirconia heads are extrinsic flaws produced by surface roughnesses of about 0.3 um Ra and that polishing these regions to about 0.1 um Ra can strongly increase the rupture load, it is believed that polishing the upper crown region to less than 0.2 um (preferably about 0.1 um) Ra will strongly increase the rupture load of the head of FIG. 2a for Cr-Co applications to provide a mean rupture load of at least 46 kN for Cr-Co applications. Therefore, there is now provided a set of 22 mm heads having a range of D values of at least 3 mm which can be fit upon a 12/14 Cr-Co or Ti alloy trunnions and possess mean rupture loads of at least 46 kN for each head.

Since the heads of the present invention should be suitable for use with Ti, stainless steel and Cr-Co trunnions, and attaining the highest rupture loads for each application likely includes polishing either the taper wall or the crown to a surface roughness Ra of about 0.1 um, it is advantageous to polish both the taper wall and the upper crown corner on a head to 0.1 um Ra to provide a YTZP head which can be used with maximum advantage both a Cr-Co or a Ti alloy trunnion. This flexibility provides yet another aspect of modularity which is so critically required for acceptance in the marketplace.

Although a 46 kN rupture load is an important attribute for FDA approval, it is not the only measure of a reliable, safe hip joint prosthesis. Another important factor is the cyclic fatigue life of the head, wherein the fitted head is subjected to a rapidly and periodically varying axial load. It is typically desirable for the head to withstand at least about 10 million cycles of the varying load without failure. The 1996 FDA draft guidelines for ceramic hip joint prosthesis requires the head to exceed 10 millions cycles of a load periodically varying between 1.4 kN and 14 kN. The 1989 FDA draft document requires the head to exceed 10 millions cycles of a load periodically varying between 4 kN and 40 kN.

Cyclic fatigue testing of the heads of FIGS. 2a–2d was carried out on Ti alloy and Cr-Co 12/14 trunnions by initially fitting the head to the trunnion with a push-on force of about 3 kN. The periodic load was varied at 15 Hz in a sinusoidal wave signal. The environment was room temperature air. The test followed the FDA recommended procedure for cyclic fatigue testing, but without the copper ring. The results of these tests are shown in Table V.

TABLE V

| Trunnion Type | Figure and D Value (mm) | | Loading (kN) | No. of Cycles To Failure |
| --- | --- | --- | --- | --- |
| Ti alloy | 2d | −0.61 | 4–40 | 10,978 |
| " | 2c | +0.39 | 4–40 | 31,878 |
|  |  |  |  | 49,475 |
| " | 2b | +2.39 | 4–40 | 10,000,000 |
| " | 2d | −0.61 | 3.5–35 | 10,786 |
|  |  |  |  | 30,386 |
|  |  |  |  | 10,000,000 |
| " | 2c | +0.39 | 3.5–35 | 118,500 |
|  |  |  |  | 10,000,000 |
| " | 2d | −0.61 | 3–30 | 10,000,000 |
| " | 2c | +0.39 | 3–30 | 10,000,000 |
|  |  |  |  | 10,000,000 |
| Cr—Co | 2d | −0.61 | 4–40 | 268,750 |
|  |  |  |  | 65,224 |
| " | 2c | +0.39 | 4–40 | 10,000,000 |
| " | 2d | −0.61 | 3–30 | 10,000,000 |
| " | 2b | +2.39 | 4–40 | 10,000,000 |

As shown in the above table, for Cr-Co trunnions, both the FIG. 2c and 2d designs exceeded 10 million cycles at 4–40 kN and 3–3 kN loads, respectively. Since experience and the above table show that the longer neck designs are much more susceptible to fatigue failure than short neck designs, it is believed the shorter neck designs (FIG. 2a) would also survive 10 million cycles at 3–30 kN when fitted upon a 12/14 Cr-Co trunnion.

Figure 5:
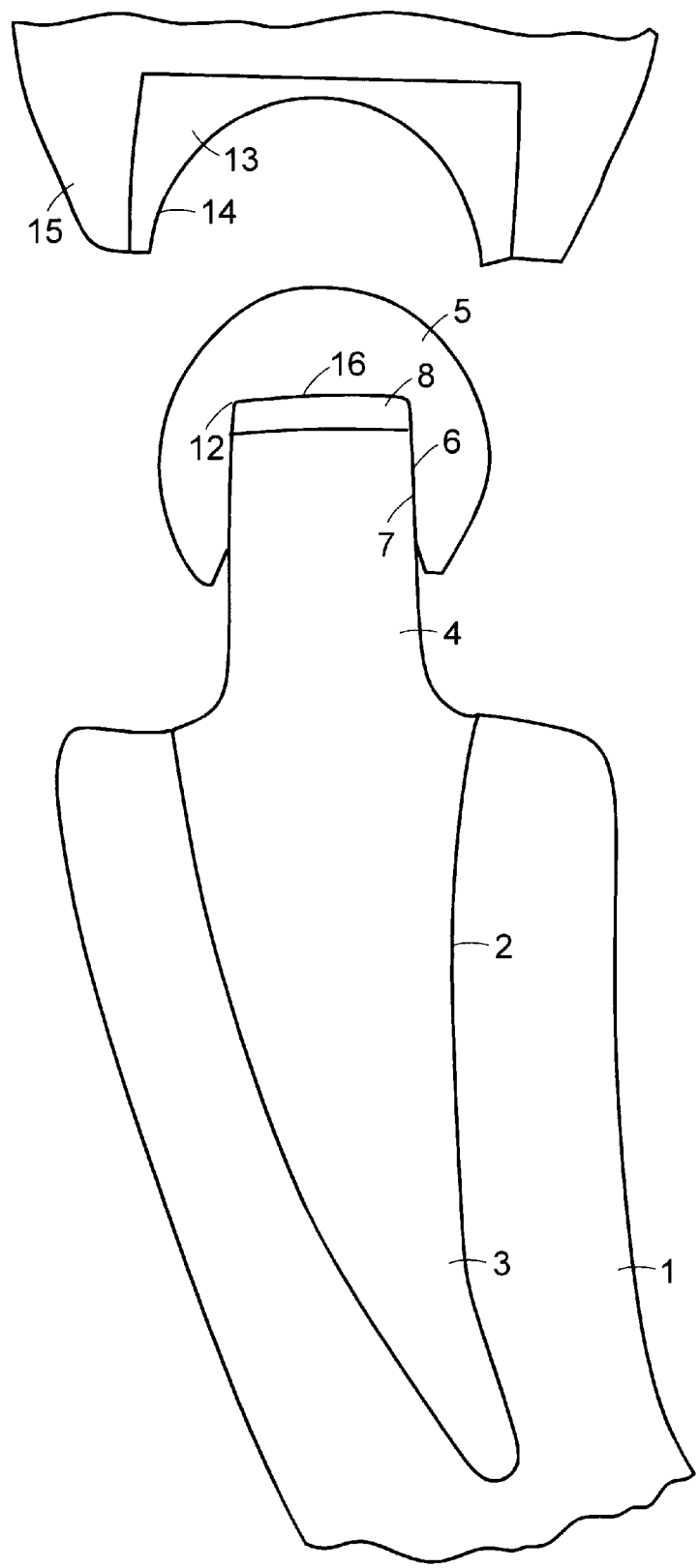
FIG. 5 presents a head of the present invention fitted to a trunnion which is fitted into a femur prior to insertion into an acetabular cup.

For Ti trunnions, each of the FIG. 2b, 2c and 2d designs exceeded 10 million cycles at loads of at least 3–30 kN. However, failure occurred much earlier in the higher load Ti applications than in their Cr-Co counterparts. Therefore, in an effort to further improve the cyclic fatigue life for the Ti applications, failure analysis of the heads fitted to Ti trunnions was undertaken. The analysis revealed that failure was occurring predominantly at the top of the chamfer (as shown by 98 in FIG. 2c). Without wishing to be tied to a theory, it is believed these failures are due to the plastic deformation of the Ti trunnion beneath the chamfer in the region shown by 99 in FIG. 2c, causing critical stresses upon the sharp corner of the chamfer (as shown in FIG. 5a) Accordingly, the head surface in this region was modified to a radius of between 5 mm and 400 mm to reduce the sharp nature of this corner. The surface roughness Ra in this area was also decreased from about 0.5 um to less than 0.3 um. One head corresponding to FIG. 2a so modified was fitted to a titanium trunnion and survived 10 million cycles at 4–40 kN. Although this test was performed on only one head, it is believed the modified chamfer can similarly eliminate the fatigue-induced stress concentration at the top of the chamfer for other head designs and thereby improve the fatigue life for Ti applications of those head designs as well.

In preferred embodiments, the head has a diameter of 22.22 mm, and has a frustoconical cavity whose total angle is about 6 degrees, preferably between 5 37' 30" and 5 43' 30", and whose opening is between about 12.2 mm and 13 mm. Its normalized radius ro/Ro is at least 0.50, typically between 0.55 and 0.60. The wall thickness should range from about 2 mm (for short neck designs) to about 5 mm (for long neck designs). The bottom chamfer should have an angle of between about 5 degrees and 45 degrees and have an axial length of between about 0.5 mm and 4 mm, preferably between about 0.5 mm and 2 mm.

Preferably, the frustocone of the trunnion has an angle substantially similar or no more than about 20' less than the angle of the frustoconical cavity. More preferably, the taper is the Euro-cone having a 12 mm diameter face which expands at a total angle of about 6 degrees to a 14 mm diameter section. Typically, the trunnion has an elastic modulus of either about 105–115 GPa (as with titanium alloys) or about 210–230 GPa (as with chrome-cobalt).

Its surface roughness Ra is typically between 0.5 um and 50 um, more typically between about 1 um and 30 um.

When the head is press fit onto the stem, it should slide down the stem and come to rest at a position whereby the reserve should range from 2 mm (for short neck designs) to about 4 mm (for long neck designs). The contact area between the head's cavity wall and the trunnion cone should be between about 150 mm2 (for long neck designs) and 450 mm2 (for short neck designs). The head component preferably consists essentially of a ceramic comprising at least about 90 mol % zirconia, and more preferably is a partially stabilized zirconia (PSZ). The PSZ is typically partially stabilized by a rare earth oxide (which includes yttria) at a concentration of between about 2 mol % and about 5 mol %. Most preferably, the PSZ is yttria stabilized tetragonal zirconia polycrystal (YTZP). Preferably, the YTZP has a mean grain size (SEM using ASTM E 112/82) of no more than 1 micron (um), preferably between 0.3 and 0.8 um. The bulk of the head should have a four point flexural strength of at least about 920 MPa, preferably at least 1300 MPa. Its density should be at least 99.7% of theoretical density, preferably at least 99.8%. In some embodiments, it has an elasticity modulus of no more than 220 GPa; an open porosity of no more than 0.1%; less than 1% impurities; and a fracture toughness (as per Chantikul) of at least 5 MPa m$^{1/2}$.

In one preferred method of making the YTZP zirconia, the rare earth oxide powder and submicron zirconia powder are mixed, the mixture is cold isostatically pressed at between 50 and 400 MPa and appropriately green machined to form a green sphere which is then sintered at between about 1300° C. and 1500° C. for about 1 to 4 hours to achieve a density of at least 95%; and the sintered piece is hipped in an inert gas such as argon at between 1300° C. and 1500° C. for between 0.5 and 4 hours to produce a sintered sphere having a density of at least 99.9%, and a grain size of at most less than one micron.

Referring now to FIG. 6, there is provided a femoral prosthesis according to the present invention. The first end 3 of metal trunnion 2 is implanted into femur 1. The second end of the trunnion 2 is shaped to a frustocone 4. The recess of the zirconia head 5 having about the same tape angle as cone 4 is press fit onto cone 4. Taper wall 6 of the head 5 defined by the frustoconical recess is in contact over its substantial length with the surface 7 of the frustocone 4. A reserve 8 between the frustocone 4 and the crown 16 is also shown. The junction of the crown 16 and the taper wall 6 is crown corner 12. Concurrently, an acetabular cup 13 having a socket surface 14 for receiving the head 5 is fitted into the pelvic bone 15. Lastly, the head 5 is positioned in the socket surface 14 of the acetabular cup 13 to form the hip joint.

We claim:

1. A kit comprising a plurality of ceramic hip joint prosthesis heads for use with a trunnion, the trunnion having a frustoconical end comprising a first section having a diameter of about 12 mm which expands inward at a total angle of about 6 degrees to form a second section having a diameter of about 14 mm, wherein each head comprises:
   a) a substantially spherical outer diameter of about 22.22 mm,
   b) a centerpoint, and
   c) a recess which forms a taper wall extending inward from the outer diameter of the head, wherein the taper wall has a shape suitable for taper fitting upon the frustoconical end of the trunnion to produce contact between the taper wall and the first section of the frustoconical end of the trunnion, a perimeter being defined by the deepest contact between the taper wall and the first section of the frustoconical end of the trunnion, the perimeter having a centerpoint, wherein each head, when taper fit upon the frustoconical end of the trunnion, has a rupture load of at least 46 kN and is characterized by a distance D between a) the centerpoint of the head and b) the centerpoint of the perimeter defined by the deepest contact between the taper wall and the first section of the frustoconical end of the trunnion,
and
wherein the range of values of D within the kit is at least 3 mm.

2. The kit of claim 1 wherein the ceramic comprises at least about 80 mol % zirconia, the trunnion is a metallic trunnion, and the end section expands to form an inner section having a diameter of about 14 mm.

3. The kit of claim 2 wherein the ceramic consists essentially of zirconia partially stabilized by between about 2 mol % and 5 mol % rare earth oxide.

4. The kit of claim 3 wherein the zirconia partially stabilized by between about 2 mol % and 5 mol % rare earth oxide has a four point flexural strength of at least 920 MPa.

5. The kit of claim 4 wherein the trunnion is Cr-Co, the recess terminates in a crown, the crown and the taper wall defining a crown corner, wherein the crown corner has a surface roughness Ra of less than 0.2 um, thereby providing improved burst strength.

6. The kit of claim 5 wherein one head has a D value of at least +4 mm.

7. The kit of claim 4 wherein the trunnion is Ti alloy and the range of D values is at least 4 mm.

8. The kit of claim 4 wherein the trunnion is Ti alloy, the head recess comprises a chamfer adjacent the outer diameter of the head, the chamfer having an innermost portion, wherein the inner most portion of the chamfer has a radius of between 5 mm and 400 mm, thereby providing improved fatigue life.

9. The kit of claim 8 wherein one head has a D value of less than +2 mm.

10. The kit of claim 4 wherein the trunnion is Ti alloy, the head recess comprises a chamfer adjacent the outer diameter of the head, the chamfer having an innermost portion, wherein the innermost portion of the chamfer has a surface roughness Ra of less than 0.3 um, thereby providing improved fatigue life.

11. The kit of claim 10 wherein one head has a D value of less than +2 mm.

12. The kit of claim 4 wherein the trunnion is Ti alloy, the taper wall has a surface roughness Ra of less than 0.2 um, and each rupture load exceeds 60 kN.

13. The kit of claim 4 wherein the trunnion is titanium and the values of D are between about +5 mm and about 0 mm.

14. The kit of claim 4 wherein the trunnion is chrome-cobalt and the values of D are between about +5 mm and about +1 mm.

15. The kit of claim 4 wherein each head is characterized by a radius of the taper wall at the centerpoint, ro/Ro, and wherein each head has an ro/Ro value of at least 0.50.

16. A substantially spherical ceramic hip joint prosthesis head for use with a titanium alloy trunnion, the trunnion having a frustoconical end which expands at a total angle of about 6 degrees, wherein the head comprises:
   a) an outer diameter, and
   b) a recess which forms a taper wall extending inward from the outer diameter of the head, wherein the taper wall has a shape suitable for taper fitting upon the frustoconical end of the trunnion, wherein the head recess comprises a chamfer adjacent the outer diameter of the head, the chamfer having an innermost portion, wherein the inner most portion of the chamfer has a radius of between 5 mm and 400 mm, thereby providing improve fatigue life when the head recess is taper fit upon the trunnion.

17. A kit comprising a plurality of ceramic hip joint prosthesis heads for use with a trunnion, the trunnion having a frustoconical end comprising a first section having a diameter of about 12 mm which expands inward at a total angle of about 6 degrees to form a second section having a diameter of about 14 mm, wherein each head comprises:
   a) a substantially spherical outer diameter of about 22.22 mm,
   b) a centerpoint,
   c) a recess which forms a taper wall extending inward from the outer diameter of the head, wherein the taper wall has a shape suitable for taper fitting upon the frustoconical end of the trunnion to produce contact between the taper wall and the first section of the frustoconical end of the trunnion, a perimeter being defined by the deepest contact between the taper wall and the first section of the frustoconical end of the trunnion, the perimeter having a centerpoint, and
   d) a radius of the taper wall at the centerpoint, ro/Ro, wherein each head has an ro/Ro value of at least 0.50.

wherein each head, when taper fit upon the frustoconical end of the trunnion is characterized by a distance D between a) the centerpoint of the head and b) the centerpoint of the perimeter defined by the deepest contact between the taper wall and the first section of the frustoconical end of the trunnion, wherein the range of values of D within the kit is at least 3 mm, and wherein the ceramic consists essentially of YTZP having a 4 point flexural strength of at least 920 MPa.

18. A ceramic hip joint prosthesis head for use with a trunnion, the trunnion having a frustoconical end comprising a first section having a diameter of about 12 mm which expands inward at a total angle of about 6 degrees to form a second section having a diameter of about 14 mm, wherein the head comprises:

a) a substantially spherical outer diameter of about 22.22 mm,
   b) a centerpoint, and
   c) a recess which forms a taper wall extending inward from the outer diameter of the head, wherein the taper wall has a shape suitable for taper fitting upon the frustoconical end of the trunnion to produce contact between the taper wall and the first section of the frustoconical end of the trunnion, a perimeter being defined by the deepest contact between the taper wall and the first section of the frustoconical end of the trunnion, the perimeter having a centerpoint, and wherein each head, when taper fit upon the frustoconical end of the trunnion, has a rupture load of at least 46 kN and is characterized by a distance D between a) the centerpoint of the head and b) the centerpoint of the perimeter defined by the deepest contact between the taper wall and the first section of the frustoconical end of the trunnion, wherein D has an absolute value of less than 2 mm.

19. The head of claim 18 wherein the trunnion is Cr-Co, the recess terminates in a crown, the crown and the taper wall defining a crown corner, wherein the crown corner has a surface roughness Ra of less than 0.2 um, thereby providing improved burst strength.

20. The head of claim 18 wherein the trunnion is Ti alloy, the head recess comprises a chamfer adjacent the outer diameter of the head, the chamfer having an innermost portion, wherein the inner most portion of the chamfer has a radius of between 5 mm and 400 mm, thereby providing improved fatigue life.

21. The head of claim 18 wherein the trunnion is Ti alloy, the head recess comprises a chamfer adjacent the outer diameter of the head, the chamfer having an innermost portion, wherein the innermost portion of the chamfer has a surface roughness Ra of less than 0.3 um, thereby providing improved fatigue life.

22. The head of claim 18 wherein the trunnion is Ti alloy, the taper wall has a surface roughness Ra of less than 0.2 um, and the rupture load exceeds 60 kN.

* * * * *